(12) United States Patent
Sato et al.

(10) Patent No.: US 7,549,337 B2
(45) Date of Patent: Jun. 23, 2009

(54) METHOD FOR INSPECTING PEELING IN ADHESIVE JOINT

(75) Inventors: Keiichi Sato, Wako (JP); Hideaki Murayama, Tokyo (JP); Kazuro Kageyama, Ushiku (JP)

(73) Assignee: Honda Motor Co., Ltd., Tokyo (JP)

( * ) Notice: Subject to any disclaimer, the term of this patent is extended or adjusted under 35 U.S.C. 154(b) by 134 days.

(21) Appl. No.: 11/783,073

(22) Filed: Apr. 5, 2007

(65) Prior Publication Data
US 2007/0237448 A1    Oct. 11, 2007

(30) Foreign Application Priority Data
Apr. 6, 2006    (JP)    ............ P2006-105650

(51) Int. Cl.
*G01N 29/04* (2006.01)
*G02B 6/00* (2006.01)
(52) U.S. Cl. .................. 73/588; 73/150 A; 73/800; 73/827; 385/12
(58) Field of Classification Search ............ 73/588, 73/150 A, 800, 827; 250/227.18, 227.14, 250/227.23; 385/12, 80
See application file for complete search history.

(56) References Cited

U.S. PATENT DOCUMENTS

| | | | | | |
|---|---|---|---|---|---|
| 4,262,990 | A | * | 4/1981 | Kamakura | ............ 359/422 |
| 4,782,492 | A | * | 11/1988 | McMahon et al. | ............ 372/34 |
| 5,250,802 | A | * | 10/1993 | Runner | ............ 250/227.15 |
| 6,616,332 | B1 | * | 9/2003 | Renken et al. | ............ 374/162 |
| 6,710,863 | B2 | * | 3/2004 | Hotate et al. | ............ 356/73.1 |
| 7,041,960 | B2 | * | 5/2006 | Sato | ............ 250/227.18 |
| 7,080,940 | B2 | * | 7/2006 | Gotthold et al. | ............ 374/161 |
| 2006/0233484 | A1 | * | 10/2006 | Van Neste et al. | ............ 385/12 |

FOREIGN PATENT DOCUMENTS

| | | | |
|---|---|---|---|
| JP | 402157620 | * | 6/1990 |
| JP | 9-101255 A | | 4/1997 |
| JP | 2001-21384 A | | 1/2001 |
| JP | 2005-98921 A | | 4/2005 |

OTHER PUBLICATIONS

Ishikawa High-resolution sensing methods using optical fiber gratings, Oyo Buturi, vol. 69, No. 06, p. 0648-0654 (2000).

* cited by examiner

*Primary Examiner*—Hezron Williams
*Assistant Examiner*—J M Saint Surin
(74) *Attorney, Agent, or Firm*—Birch, Stewart, Kolasch & Birch, LLP

(57) ABSTRACT

A method is disclosed wherein a portion of a sensor part of an optical fiber sensor is embedded in an adhesive between two joined members, and peeling in an adhesive joint of the two members is detected on the basis of measuring optical characteristics from the optical fiber sensor when the optical fiber sensor is irradiated with light from a light source while one member is vibrated by vibration means. The method comprises the steps of determining the temperature of the two members during measurement on the basis of the optical characteristics from the sensor part exposed outside of the adhesive; determining, on the basis of the temperature determined during the measurement, the measurement range in which the optical characteristics from the optical fiber sensor are measured; and measuring the variation in the optical characteristics from the optical fiber sensor within the determined measurement range while the member is being vibrated by the vibration means.

11 Claims, 12 Drawing Sheets

METHOD FOR INSPECTING PEELING IN ADHESIVE JOINT

FIELD OF THE INVENTION

The present invention relates to a method for inspecting peeling in an adhesive joint and, more particularly, to a method for inspecting peeling in an adhesive joint by using an optical fiber sensor.

BACKGROUDN OF THE INVENTION

In conventional practice an inspector inspects the soundness of an adhesive joint between two members by looking for minute cracks in the adhesive joint with the naked eye or by ultrasonic flaw detection. However, even when a skilled inspector inspects the adhesive joint with the naked eye, it is difficult to make an inspection without any oversights, and the number of steps increases. Various sensors are used to conduct tests for evaluating the soundness of an adhesive joint, but this is impractical because of the difficulty of drawing conclusions and because of problems with the precision of inspection. To resolve such problems, a technique has been devised wherein the sensor part of an optical fiber sensor is embedded in the adhesive joint of joined members (a pair composed of two bonded members), and is bonded in proximity to the adhesive joint to measure the joining state of the joined members.

The term "optical fiber sensor" refers to an optical fiber in which a sensor part is formed in part of the core. The sensor part is a diffraction grating, for example. An optical fiber sensor comprising a diffraction grating is referred to as an "optical fiber grating sensor." The configuration of the sensor part is not limited to a diffraction grating. With an optical fiber sensor, the joining state is measured using changes in optical characteristics resulting from strain in the sensor part.

When the joining state is measured using an optical fiber sensor, the sensor part of the optical fiber sensor is attached to the inside of an adhesive between two members that are bonded with the adhesive. Output light from a broadband light source falls on the light-incident part of the optical fiber sensor, and changes are observed in the light reflected from the sensor part and the light transmitted by the sensor part. The joining state between the two members is determined from this observation. This measurement is disclosed in JP-A-09-101255 and JP-A-2001-21384, for example.

In a conventional method for inspecting an adhesive joint by using an optical fiber sensor, when peeling occurs in the adhesive joint either in or near the portion in which the sensor part of the optical fiber sensor is embedded, the peeling in the adhesive joint is detected according to changes in the reflected light or transmitted light from the sensor part of the optical fiber sensor. However, problems are encountered in that peeling is difficult to detect when peeling occurs in the adhesive joint at a location distanced from the sensor part embedded in the adhesive joint.

In view of this, JP-A-2005-98921 discloses a configuration wherein the sensor part of the optical fiber sensor is attached to the adhesive joint of the two members, and a vibrating piezoelectric element is bonded to the surfaces of the joined members. To inspect the joining state, the inspector operates the piezoelectric element to create vibration in the joined members, and detects the characteristics of the reflected light from the optical fiber sensor at the time.

A precise measuring technique based on an optical fiber sensor is disclosed in "Precise Measuring Technique Based on Optical Fiber Grating" by Shinji Ishikawa, Applied Physics, Vol. 69, pg. 6 (2000), lines 648-654.

JP-A-2005-98921 also discloses a configuration of a measuring apparatus that can detect peeling in an adhesive joint at a location distanced from the position of the optical fiber sensor embedded in the adhesive joint. In this measuring apparatus, a vibrating device is attached to the surface of the joined members, and the vibrating device is operated to vibrate the joined members while vibration is measured at the peak position of the spectrum of reflected light obtained from the optical fiber sensor. When this measurement is taken, a measurement window in the measuring apparatus must be provided so that the peak is within the range of measurement.

The peak of the spectrum of reflected light from the optical fiber sensor varies depending on the temperature of the joined members. This is believed to be the result of the fact that strain in the optical fiber sensor varies with temperature due to the effects of thermal expansion in the optical fiber sensor or the joined members. Therefore, in cases in which the aforementioned measurement window is provided and fixed in place, problems are encountered in that depending on temperature, vibration is no longer observed in the peak position of the spectrum of reflected light from the optical fiber sensor.

Therefore, there is a demand to make it possible to easily observe vibration in the peak position of the spectrum of reflected light from the optical fiber sensor despite changes in temperature conditions, or to observe vibration in the dip position of the spectrum of transmitted light from the optical fiber sensor; and to establish a method for inspecting peeling in an adhesive joint, wherein peeling in an adhesive joint can be accurately inspected.

SUMMARY OF THE INVENTION

According to one aspect of the present invention, there is provided a peeling inspection method wherein at least one member selected from at least two members joined using an adhesive is provided with vibration means, a portion of a sensor part of an optical fiber sensor is embedded in the adhesive for joining the two members, and peeling in an adhesive joint of the two or more members is detected on the basis of optical characteristics from the optical fiber sensor when the optical fiber sensor is irradiated with light from a light source while the member is vibrated by the vibration means, the method comprising the steps of: determining a temperature of the two members during measurement on the basis of the optical characteristics from that portion of the sensor part which is exposed outside of the adhesive; determining, based on the temperature determined during the measurement, a measurement range in which the optical characteristics from the optical fiber sensor are measured; vibrating the member by means of the vibration means; and measuring the variation in the optical characteristics from the optical fiber sensor within the determined measurement range while the member is being vibrated by the vibration means.

In this arrangement, one of the two joined members is provided with a piezoelectric element (vibration means), a portion of the sensor part of the optical fiber sensor is embedded in the adhesive in the adhesive joint, and peeling in the adhesive joint is detected on the basis of the optical characteristics from the optical fiber sensor when the optical fiber sensor is irradiated with light from the light source while the member is being vibrated by the vibration means. When vibration is applied, the variation is measured in the optical characteristics from the optical fiber sensor within the determined measurement range. Vibration of the peak position of the spectrum of reflected light from the optical fiber sensor can thereby be easily measured at various temperatures, and peeling in the adhesive joint can be accurately inspected. Not only can peeling be detected at the position of the optical fiber sensor embedded in the adhesive and in proximity thereof, but peeling can also be precisely detected at positions distanced from the optical fiber sensor. Therefore, it is possible to accurately conclude whether peeling has or has not occurred. Situations can accordingly be prevented in which peeling is erroneously detected despite the fact that no peeling has occurred in practical terms, and the structure is needlessly disassembled. Specifically, maintenance costs for the structure can be reduced, and improvements in the stability of the structure can be expected.

The peeling inspection method may be applied to inspect peeling in an adhesive joint in the frame of an aircraft.

Preferably, the peeling inspection method also comprises, in addition to the step for vibrating the member by the vibration means, a step for applying a specific load from the member side.

Desirably, the specific load is an external force that elastically deforms the joined members composed of at least two members joined by the adhesive.

The optical fiber sensor may be an optical fiber grating sensor.

The optical characteristics may be reflected light characteristics.

It is preferred that the adhesive be a room-temperature curing adhesive.

BRIEF DESCRIPTION OF THE DRAWINGS

Certain preferred embodiments of the present invention will be described in detail below, by way of example only, with reference to the accompanying drawings, in which.

DESCRIPTION OF THE PREFERRED EMBODIMENTS

The method for inspecting peeling in an adhesive joint according to an embodiment of the present invention comprises a database creation step (step S1 shown in FIG. 1) for creating data related to the spectrum of reflected light in relation to temperature and obtained both from an optical fiber sensor whose sensor part is embedded in an adhesive in joined members composed of two members joined using the adhesive, and from an optical fiber sensor whose sensor part is not embedded in the adhesive; and a peeling inspection step (step S2 shown in FIG. 10) related to actual peeling in the adhesive joint. The database creation step and the peeling inspection step are described hereinbelow with reference to the drawings.

Figure 1:
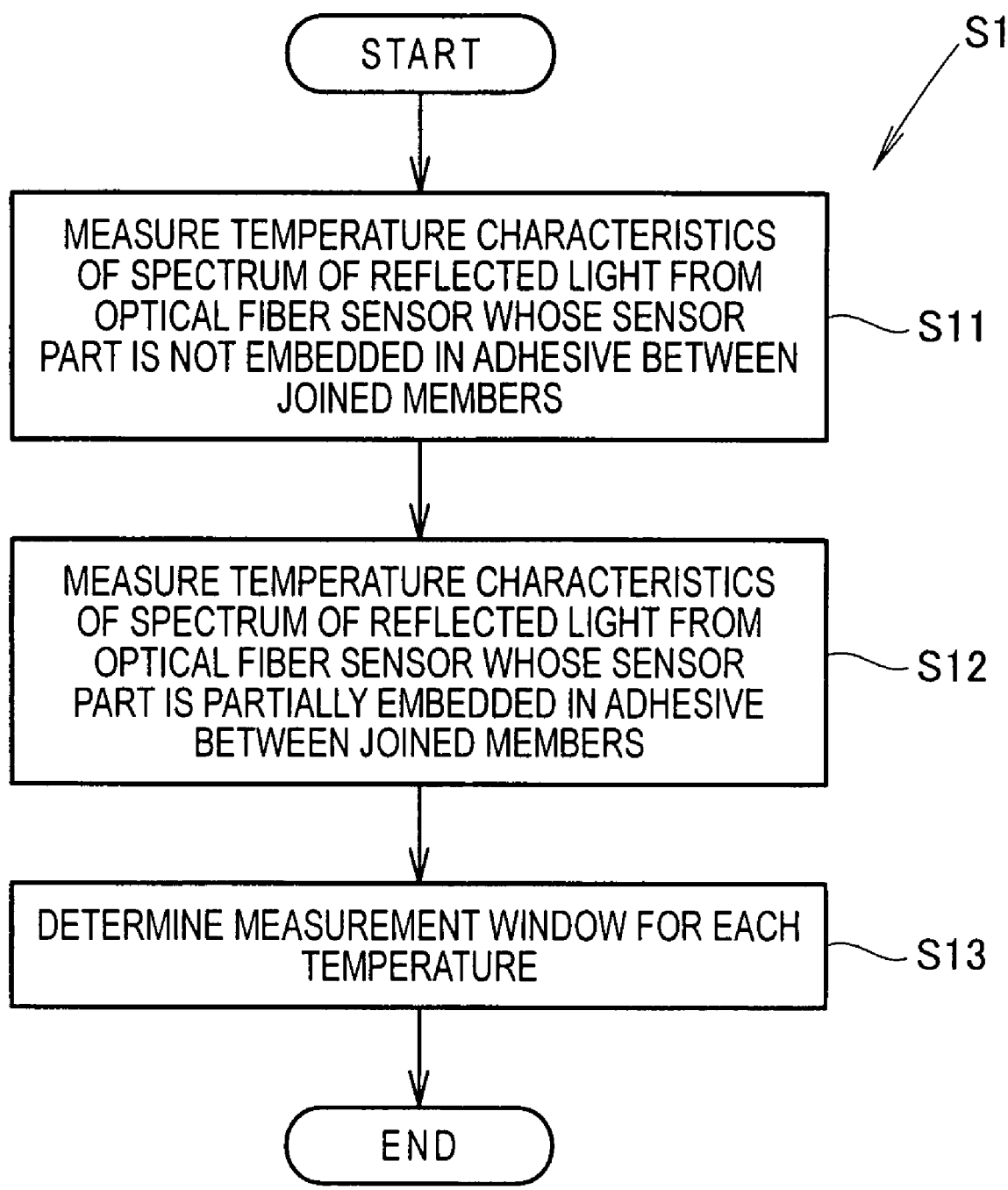
FIG. 1 is a flowchart showing a database creation step.

The database creation step S1 is described with reference to the flowchart in FIG. 1. The database creation step S1 has a measuring step S11 for measuring the temperature characteristics of the spectrum of reflected light from a free optical fiber sensor whose sensor part is not embedded in an adhesive between joined members, a measuring step S12 for measuring the temperature characteristics of the spectrum of reflected light from an optical fiber sensor whose sensor part is partially embedded in an adhesive between joined members, and a determination step S13 for determining a measurement window for each temperature.

Figure 2:
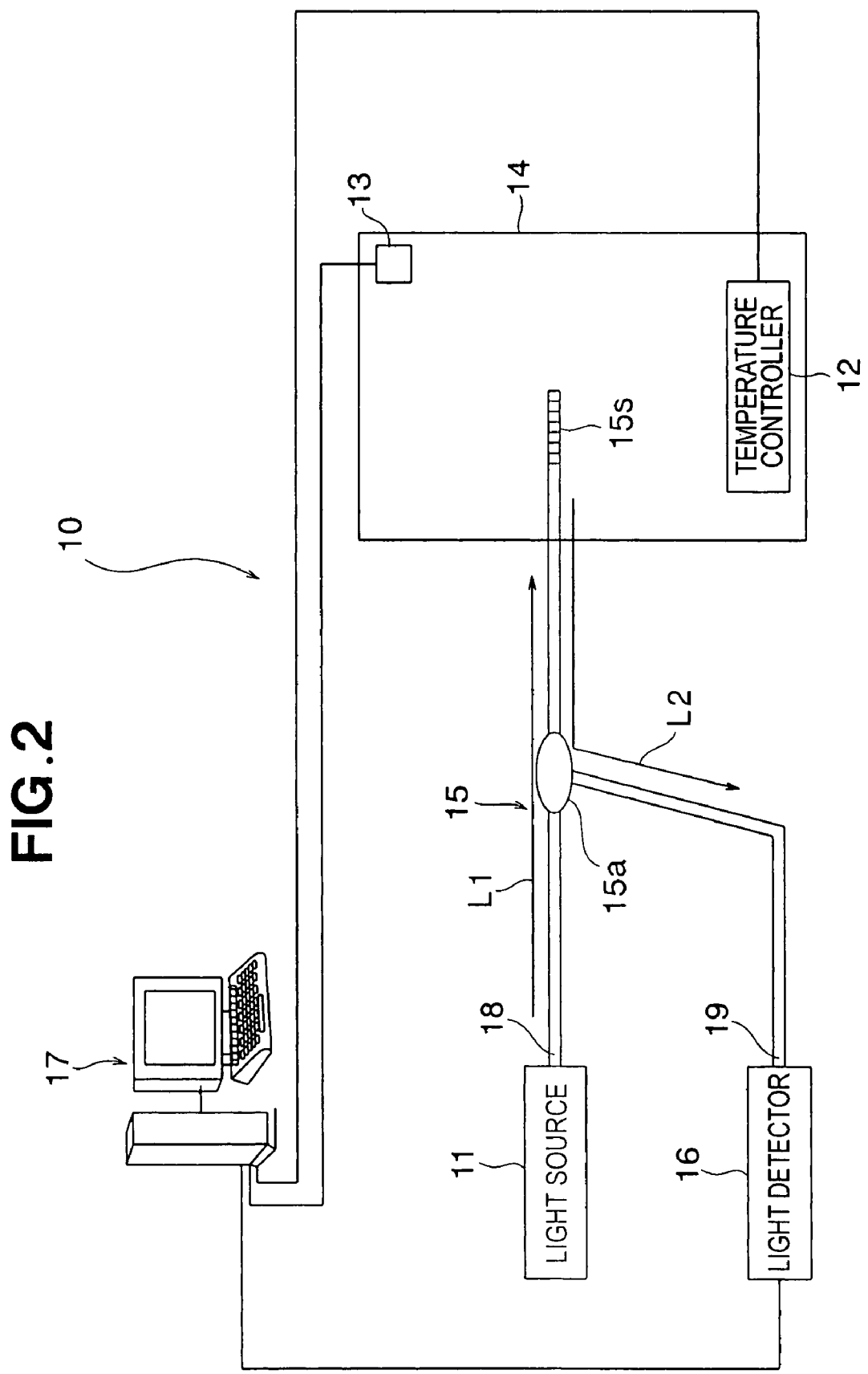
FIG. 2 is a diagrammatical view illustrating a measurement system used in a step for measuring the temperature characteristics of the reflected spectrum of a free optical fiber sensor that is not embedded in an adhesive between joined members.

The following is a description, made with reference to the measurement system shown in FIG. 2, of the step S11 for measuring the temperature characteristics of the spectrum of reflected light from an optical fiber sensor whose sensor part is not embedded in an adhesive between joined members. The measurement system 10 shown in FIG. 2 has a light source 11, an optical fiber sensor 15 in which a sensor part 15s is disposed in a thermostat 14 having a temperature controller 12 and a temperature sensor 13; a light detector 16; and a computer 17.

The light source 11 is a device for illuminating an end surface 18 on the light-incident side of the optical fiber sensor 15 with broadband light. The light source 11 emits light of a wavelength in a range that includes light of a wavelength that can be detected by the optical fiber sensor 15. The light source 11 is a light source having a broadband continuous spectrum, such as a super-luminescent diode (SLD), a halogen lamp, or a tungsten lamp, for example.

The optical fiber sensor 15 is configured using an optical fiber, and the sensor part 15s is formed using the core at the end of the optical fiber. The optical fiber sensor 15 is provided with a coupler 15a in the middle of the optical fiber sensor. The sensor part 15s is formed as part of the optical fiber. In the optical fiber sensor 15, light from the light source 11 is guided to one end of the optical fiber, and the light from the light source 11 is directed to the sensor part 15s via the optical fiber (incident light L1). The reflected light L2 from the sensor part 15s is directed toward the light detector 16 via the coupler 15a, and is detected by the light detector 16. An optical fiber grating sensor, for example, is used as the optical fiber sensor 15. In an optical fiber grating sensor, a diffraction grating is provided as the sensor part, and the optical characteristics of the diffraction grating are utilized. In the following description, an example is described in which an optical fiber grating sensor is used as the optical fiber sensor 15. The proximal end 18 of the optical fiber is connected to the light source 11, and the sensor part 15s is provided to the distal end. The sensor part 15s is a diffraction grating formed in the core of the optical fiber, as will be described later. The sensor part 15s is placed inside the thermostat 14. The distal end 19 of the optical fiber that branches off from the coupler 15a is connected to the light detector 16.

A specific temperature is maintained inside the thermostat 14 by the temperature controller 12 connected to the computer 17. The thermostat 14 can be controlled to various temperatures. The temperature inside the thermostat 14 is measured by the temperature sensor 13, and the measured temperature is stored in memory in the computer 17.

An optical spectrum analyzer, for example, is used as the light detector 16 shown in FIG. 2 in order to obtain the spectrum of reflected light from the sensor part 15s.

Figure 3:
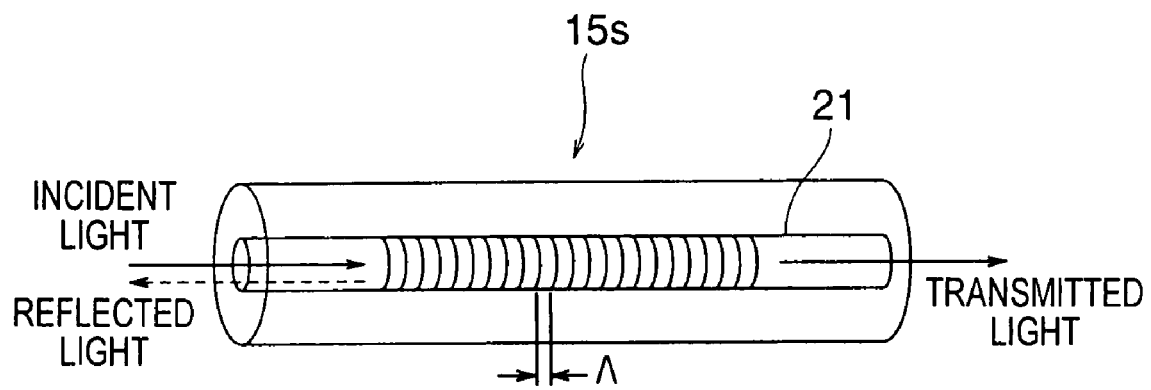
FIG. 3 is a schematic view showing the configuration of a sensor part containing a diffraction grating.

The following is a description, made with reference to FIG. 3, of the principle of measuring the temperature characteristics of the spectrum of reflected light from an optical fiber sensor whose sensor part is not embedded in an adhesive between joined members in the measurement system 10.

FIG. 3 is a schematic view of a sensor part of an optical fiber grating sensor. In the sensor part 15s of the optical fiber grating sensor used as the optical fiber sensor 15, a period on the order of the wavelength of light is stored in a fiber core 21 by periodically varying the refractive index of the core. The sensor part 15s is therefore provided with a function for reflecting light of a specific wavelength by using coupling between forward and reverse modes of propagation through the core 21. The coupling wavelength $\lambda_B$ can be expressed as Eq. (1) by using the effective refractive index $n_{core}$ and the refractive index period $\Lambda$ of the propagation mode.

$$\lambda_B = 2 n_{core} \Lambda \tag{1}$$

Reflectivity R can be calculated from Eq. (2) by using the refractive index change $\Delta n$, the grating length L, and the confinement rate $\eta c$ of propagated light in the core.

$$R_B = \tan h^2(\pi L \cdot \Delta n \cdot \eta c / \lambda B) \tag{2}$$

Figure 5:
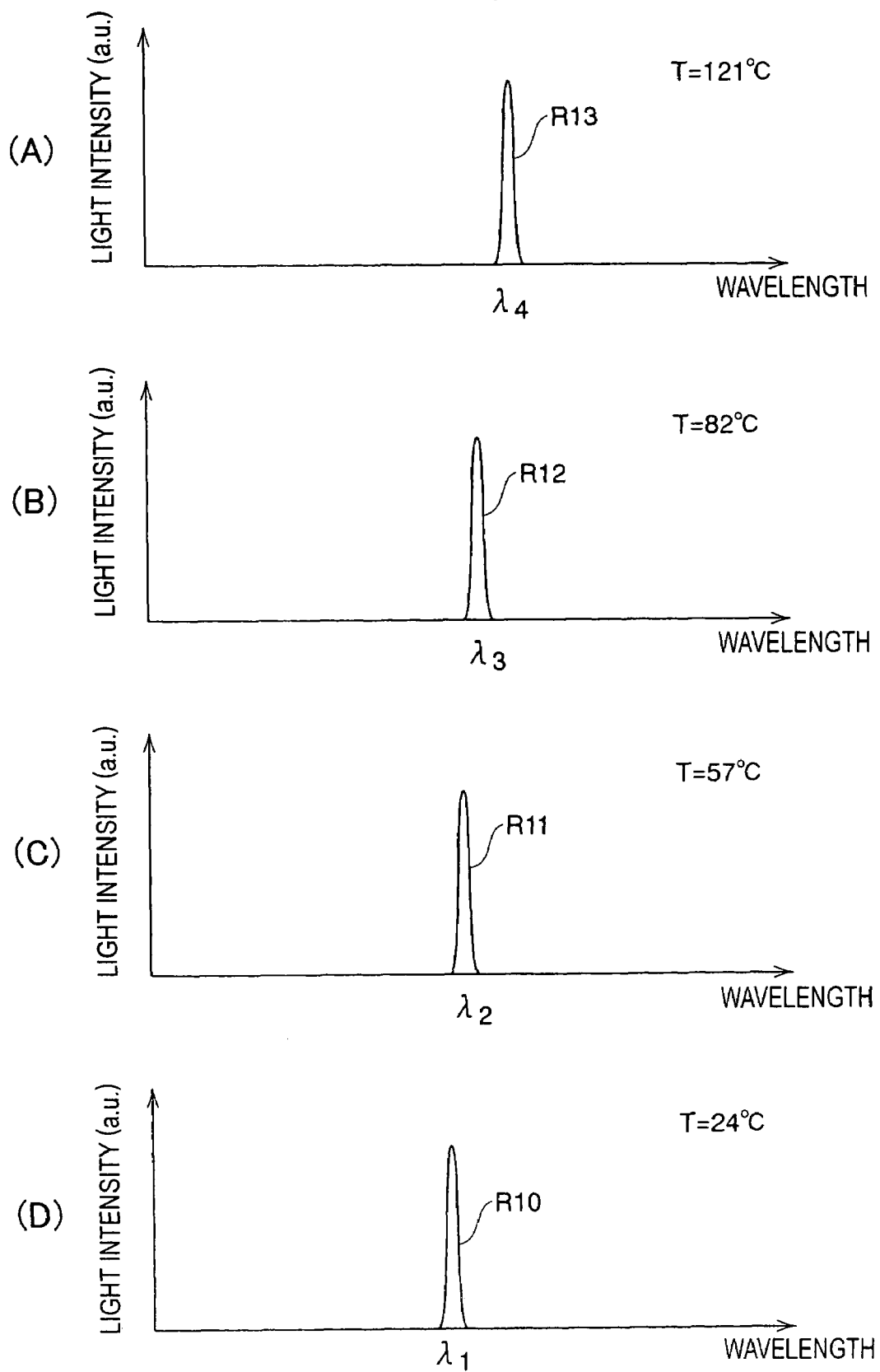
FIG. 5 is a characteristic diagram showing an example of characteristic data (light intensity) that depends on the temperature (121° C., 82° C., 57° C., 24° C.) of the reflected spectrum of a free optical fiber sensor, as measured using the measurement system shown in FIG. 2.

For example, in the case of an optical fiber grating used to separate the wavelengths of a multiplex transmission in a 1.55-μm band, the refractive index period $\Lambda$ is about 0.5 μm, the grating length L is 10 mm, the refractive index period $\Lambda$ is stored for about 20,000 layers, and extremely steep reflected light characteristics are obtained, as shown in FIG. 5.

Figure 4:
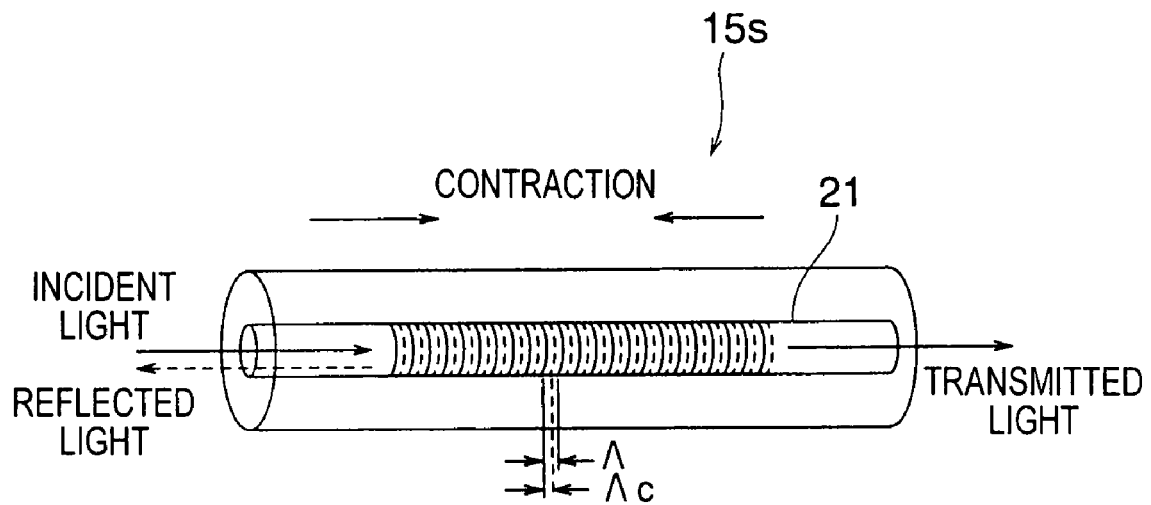
FIG. 4 is a schematic view showing a state in which the temperature of the diffraction grating changes and the sensor part undergoes thermal contraction.

The sensor part 15s undergoes thermal contraction (or expansion) when the temperature of the sensor part 15s changes. When the sensor part 15s undergoes thermal contraction, the refractive index period $\Lambda$ decreases to "$\Lambda c$" as shown in FIG. 4, and the coupling $\lambda_B$ decreases according to Eq. (1). Specifically, there is a decrease in the wavelength of the reflected light. When the sensor part 15s undergoes thermal expansion, the result is the opposite of the one described above. The peak wavelength of the spectrum of reflected light from the sensor part 15s therefore shifts depending on the temperature.

By observing the spectrum of the reflected light with the aid of the measurement system 10 on the basis of the principles described above, it is possible to obtain data on the temperature characteristics of the spectrum of reflected light from the free optical fiber sensor whose sensor part is not embedded in the adhesive between the joined members.

FIG. 5 shows an example of data on the temperature characteristics of the reflection spectrum of the free optical fiber sensor 15, as measured using the measurement system 10 shown in FIG. 2.

The horizontal axes in graphs (A) through (D) in FIG. 5 represent wavelength, and the vertical axes represent light intensity (a.u.). At T=24° C., as shown in graph (D), the spectrum R10 of the reflected light has a peak at a wavelength $\lambda 1$. At T=57° C., as shown in graph (C), the spectrum R11 of the reflected light has a peak at a wavelength $\lambda 2$ ($\lambda 2 > \lambda 1$). At T=82° C., as shown in graph (B), the spectrum R12 of the reflected light has a peak at a wavelength $\lambda 3$ ($\lambda 3 > \lambda 2$). At T=121° C., as shown in graph (A), the spectrum R13 of the reflected light has a peak at a wavelength $\lambda 4$ ($\lambda 4 > \lambda 3$). The peak wavelength of the reflection spectrum shifts towards longer wavelengths with increased temperature, as shown in graphs (A) through (D). The spectra of reflected light at all temperatures, including this data, are stored in memory in the computer 17, and a database is created.

Figure 6:
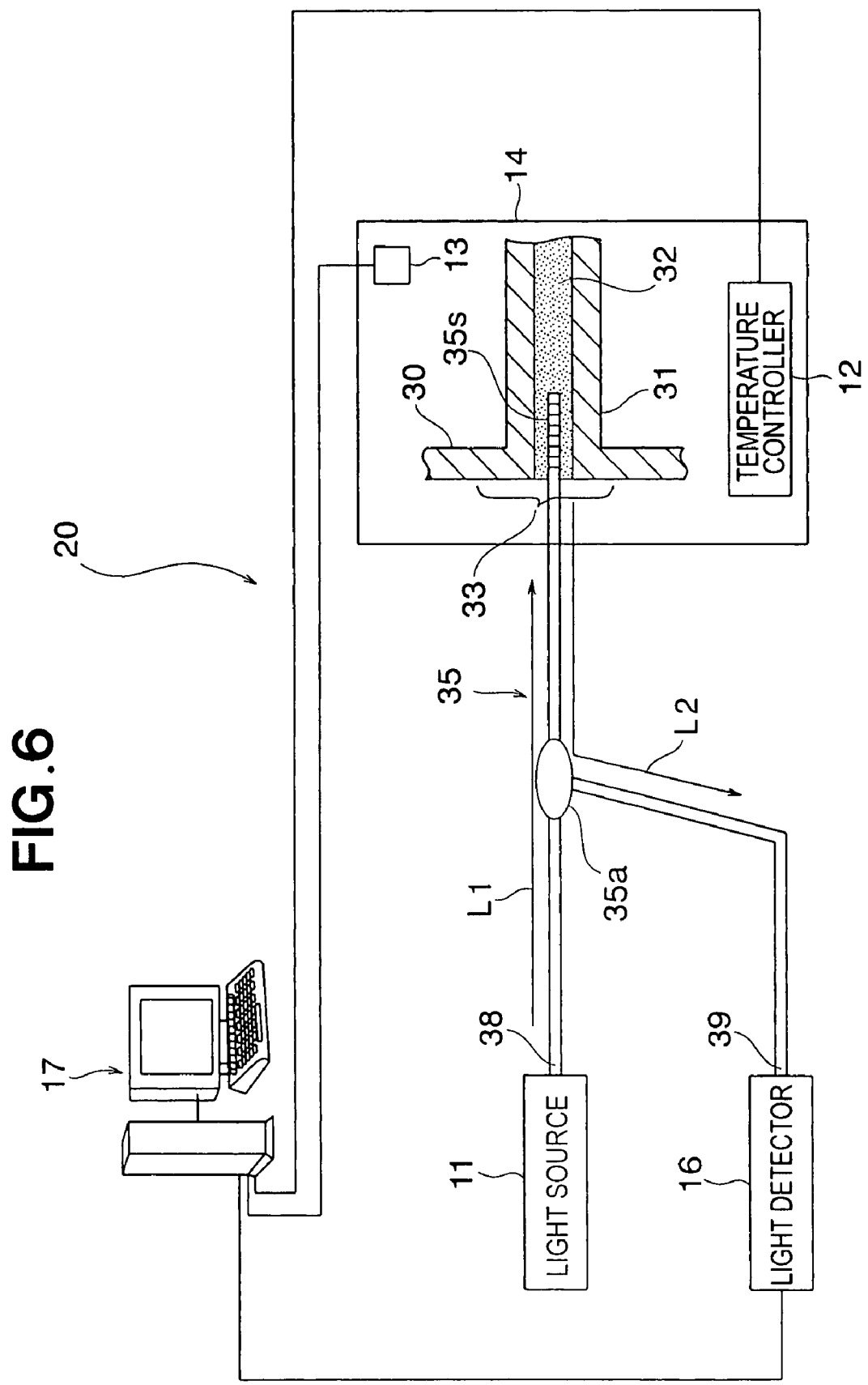
FIG. 6 is a diagrammatical view illustrating a measurement system used in the step for measuring the temperature characteristics of the reflected spectrum of an optical fiber sensor whose sensor part is partially embedded in an adhesive joint between joined members.

The following is a description, made with reference to the measurement system shown in FIG. 6, of the step S12 of measuring the temperature characteristics of the spectrum of reflected light from an optical fiber sensor whose sensor part is partially embedded in the adhesive between the joined members. In FIG. 6, the same numerical symbols are used to denote substantially similar elements as those in the apparatus described in FIG. 2 in relation to the previously described measuring step S11, and these elements are not described in detail herein.

In FIG. 6, a measurement system 20 has a light source 11; a thermostat 14 having a temperature controller 12 and a temperature sensor 13; joined members composed of two members 30, 31 joined using an adhesive 32; an optical fiber sensor 35 having a sensor part 35s embedded in the adhesive 32; a light detector 16; and a computer 17.

The portion indicated by the reference numeral 33 in FIG. 6 is an adhesive joint formed by joining the two members 30, 31 with the aid of the adhesive 32.

The joined members formed by joining the two members 30, 31 are disposed inside the thermostat 14. The sensor part 35s is formed at the distal end of the optical fiber sensor 35.

The optical fiber sensor 35 is configured using an optical fiber, the sensor part 35s is formed using the core at one end of the optical fiber, and a coupler 35a is provided in the middle of the optical fiber. The sensor part 35s is formed as part of the optical fiber. In the optical fiber sensor 35, light from the light source 11 is guided to one end of the optical fiber, and the light from the light source 11 is directed to the sensor part 35s via the optical fiber (incident light L1). The reflected light L2 from the sensor part 35s is directed toward the light detector 16 via the coupler 35a, and is detected by the light detector 16. An optical fiber grating sensor, for example, is used as the optical fiber sensor 35. In the following description, an example is described in which an optical fiber grating sensor is used as the optical fiber sensor 35. The proximal end 38 of the optical fiber is connected to the light source 11, and the sensor part 35s is provided at the distal end. The sensor part 35s is a diffraction grating formed in the core of the optical fiber. A portion of the sensor part 35s is embedded in the adhesive 32 when the two members 30, 31 are joined to each other, and the remaining portion is disposed outside of the adhesive 32. The members 30, 31 (joined members), in which the sensor part 35s is embedded in the adhesive 32, are disposed inside the thermostat 14. The distal end 39 of the optical fiber that branches off from the coupler 35a is connected to the light detector 16.

Figure 7:
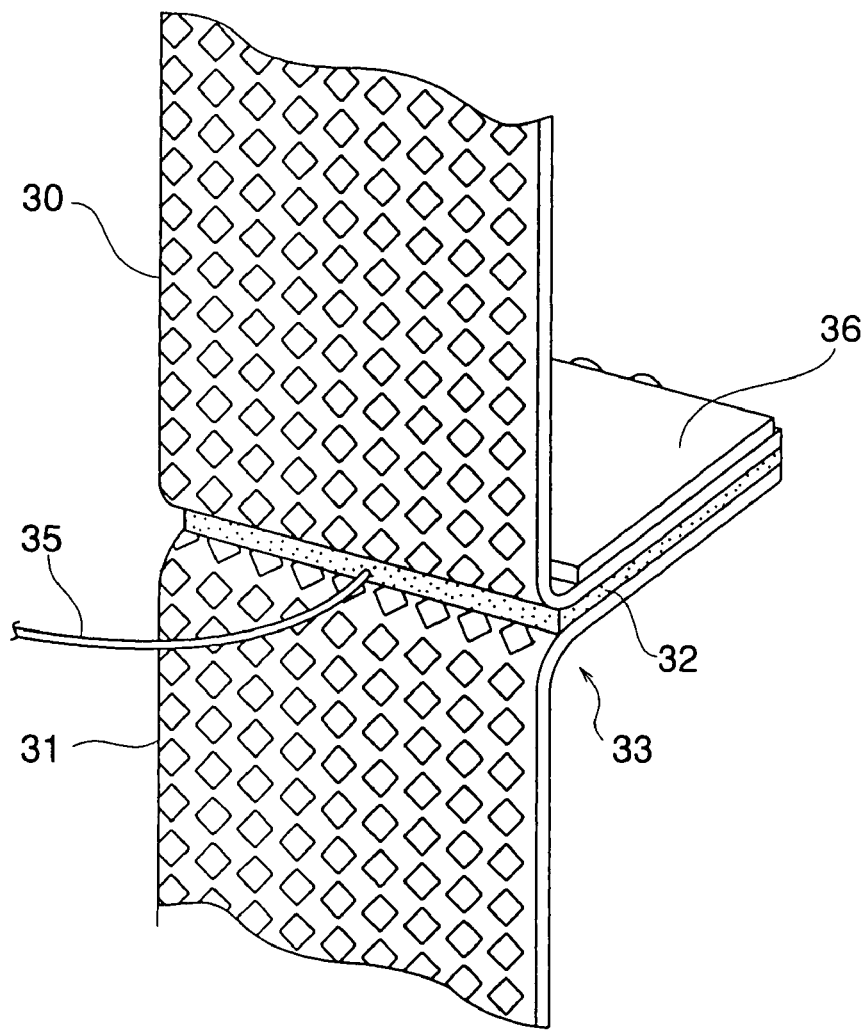
FIG. 7 is a perspective view of the sensor part embedded in the adhesive of the adhesive joint.
Figure 8:
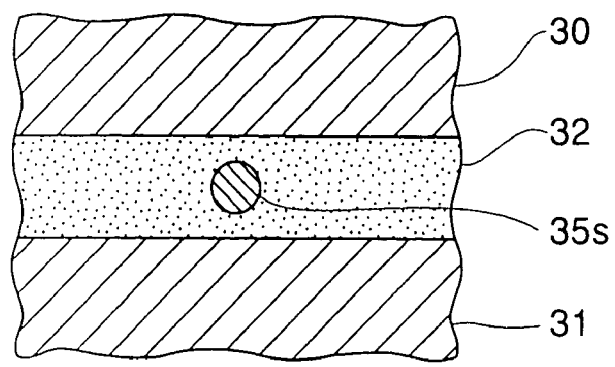
FIG. 8 is an enlarged longitudinal cross-sectional view of the portion in which the sensor part is embedded in the adhesive of the adhesive joint.

In the joined members composed of the two members 30, 31 joined using the adhesive 32, the sensor part 35s at the distal end of the optical fiber sensor 35 is about halfway inserted and embedded in the adhesive 32, as shown in FIG. 7. The sensor part 35s is disposed at an estimated intermediate position in the thickness direction of the adhesive 32, as shown in FIG. 8.

portion in which the sensor part 35s is embedded in the adhesive joint 33 is in proximity to the surface exposed in the outside of the adhesive 32 that forms the adhesive joint 33. This area in proximity to the surface is subject to cracking and peeling in the adhesive joint 33. The sensor part 35s is preferably secured in the adhesive 32 by exposing half of the sensor part 35s from the end of the grating on the light-incident side to the outside of the adhesive 32, and leaving the remaining half embedded. Furthermore, in FIG. 7, a piezoelectric element 36 used as a vibration device in the peeling inspection step is attached to the joined portion of the member 30, which positioned on top.

When the sensor part 35s of the optical fiber sensor 35 is embedded in the adhesive 32, a room-temperature curing adhesive is used as the adhesive 32 for joining the two members 30, 31.

The following is a description of the principle of measuring the temperature characteristics of the reflection spectrum of the optical fiber sensor 35 in the measurement system 20.

The structure of the fiber grating of the sensor part 35s of the optical fiber sensor embedded in the adhesive 32 between the joined members composed of the two members 30, 31 is the same as the structure of the sensor part 15s described in FIG. 3. A period on the order of light is stored in a fiber core of the sensor part 35s, and the sensor part 35s has a function for reflecting light of a specific wavelength by using coupling between the forward and reverse modes of propagation through the fiber core. The coupling wavelength $\lambda_B$ is expressed by Eq. (1) above by using the effective refractive index $n_{core}$ and the refractive index period $\Lambda$ of the propagation mode. Reflectivity R can be calculated from Eq. (2) by using the refractive index change $\Delta n$, the grating length L, and the confinement rate $\eta c$ of propagated light in the core.

In the measurement system 20, half of the sensor part 35s is embedded in the adhesive 32, and the remaining half of the sensor part 35s is not embedded in the adhesive 32.

When the temperature of the diffraction grating of the sensor part 35s changes, the sensor part 35s undergoes thermal contraction (or expansion), the refractive index period $\Lambda$ decreases (or increases), and the coupling $\lambda_B$ decreases (or increases) according to Eq. (1); i.e., the wavelength of the reflected light decreases (or increases). The peak wavelength of the spectrum of reflected light from the sensor part 35s therefore shifts depending on the temperature. The manner in which the peak wavelength shifts according to temperature is different in the portion of the sensor part 35s embedded in the adhesive 32, and in the portion of the sensor part 35s not embedded in the adhesive 32. This is because the portion of the sensor part 35s embedded in the adhesive 32 is also affected by the thermal contraction or thermal expansion of the adhesive 32.

By observing the spectrum of the reflected light from the sensor part 35s with the aid of the measurement system 20 on the basis of the principles described above, it is possible to obtain data on the temperature characteristics of the spectrum of reflected light from the optical fiber sensor 35 whose sensor part 35s is halfway embedded in the adhesive 32 in the adhesive joint 33 between the joined members.

Figure 9:
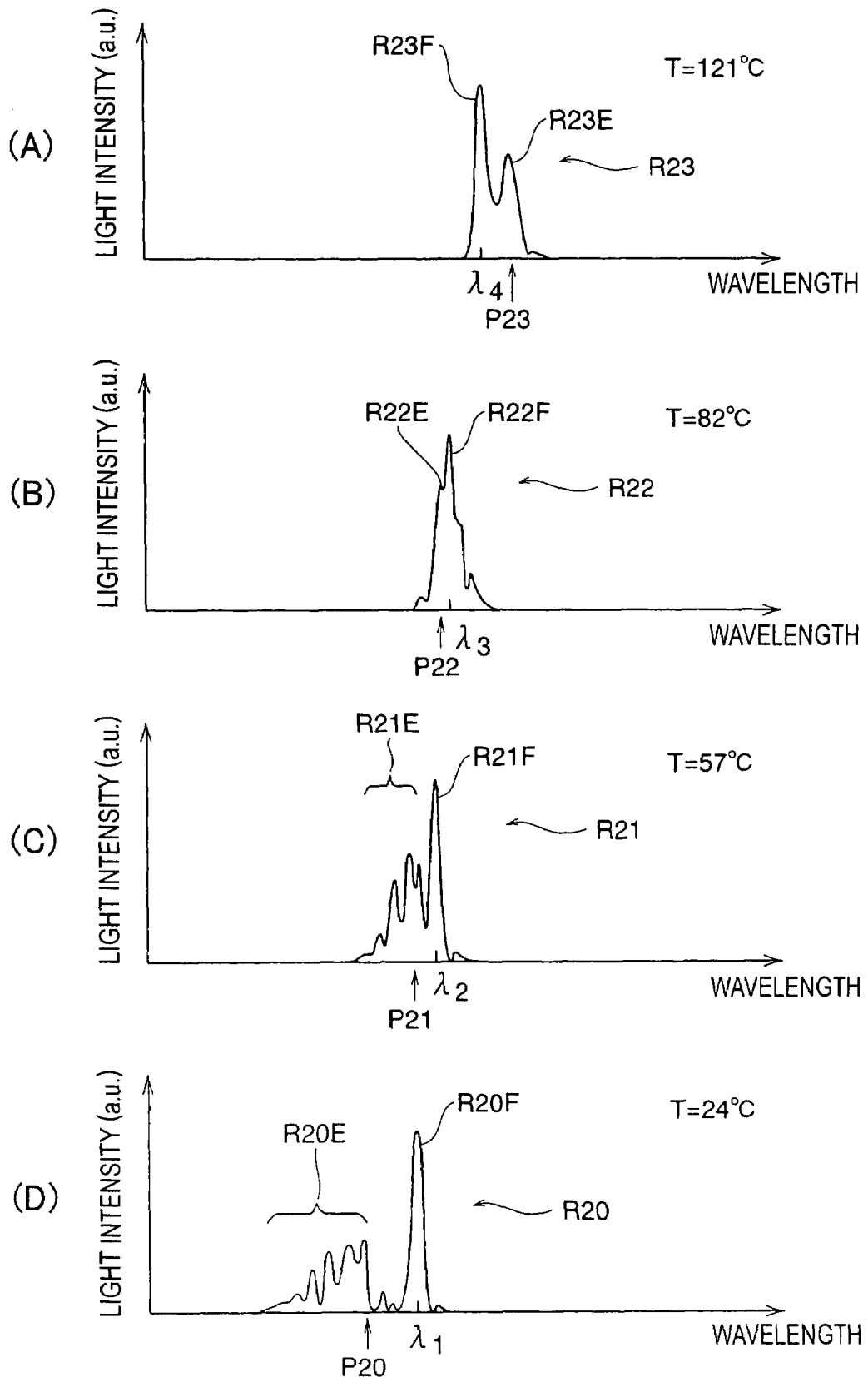
FIG. 9 is a characteristic diagram showing an example of characteristic data (light intensity) that depends on the temperature (121° C., 82° C., 57° C., 24° C.) of the reflected spectrum of an optical fiber sensor whose sensor part is halfway embedded in the adhesive joint, as measured using the measurement system shown in FIG. 6.

FIG. 9 shows an example of data on the temperature characteristics of the reflection spectrum of the optical fiber sensor 35, as measured using the measurement system 20 shown in FIG. 6.

The horizontal axes in graphs (A) through (D) in FIG. 9 represent wavelength, and the vertical axes represent light intensity (a.u.). The description below proceeds from lower temperatures T.

The data at T=24° C. shown in graph (D) is a spectrum R20 of reflected light. This spectrum R20 is composed of a spectrum R20E of reflected light from the sensor part embedded in the adhesive 32, at a shorter wavelength than the wavelength λ1, and a spectrum R20F of reflected light that has a peak at the wavelength λ1 and is obtained from the sensor part not embedded in the adhesive 32.

The data at T=57° C. shown in graph (C) is a spectrum R21 of reflected light. This spectrum R21 is composed of a spectrum R21E of reflected light from the sensor part embedded in the adhesive 32, at a shorter wavelength than the wavelength λ2, and a spectrum R21F of reflected light that has a peak at the wavelength λ2 (λ2>λ1) and is obtained from the sensor part not embedded in the adhesive 32.

The data at T=82° C. shown in graph (B) is a spectrum R22 of reflected light. This spectrum R22 is composed of a spectrum R22E of reflected light from the sensor part embedded in the adhesive 32, at a wavelength near λ3, and a spectrum R22F of reflected light that has a peak at the wavelength λ3 (λ3>λ2) and is obtained from the sensor not embedded in the adhesive 32.

The data at T=121° C. shown in graph (A) is a spectrum R23 of reflected light. This spectrum R23 is composed of a spectrum R23E of reflected light from the sensor part embedded in the adhesive 32, at a longer wavelength than the wavelength λ4, and a spectrum R23F of reflected light that has a peak at the wavelength λ4 (λ4>λ3) and is obtained from the sensor part not embedded in the adhesive 32.

As described above, as the temperature of the sensor part 35s increases, the peak wavelength of the spectrum of reflected light from the sensor part 35s shifts toward longer wavelengths. Data of the spectra of reflected light at all temperatures, including this data, is stored in memory in the computer 17, and a database is created.

In the actual peeling inspection step S2 for the adhesive joint 33, vibration is induced in the joined members by the piezoelectric element 36, and the vibration is measured at a specific wavelength (based on the reflection spectrum shown in FIG. 9) of the reflection spectrum from the sensor part 35s embedded in the adhesive 32 of the adhesive joint 33.

The wavelength used for this measurement must be determined in order to perform this measurement.

However, the spectrum of reflected light from the portion of the sensor part 35s embedded in the adhesive 32 varies in wavelength depending on temperature, as shown in FIG. 9. Therefore, the wavelength (measurement window) to be measured must be set according to the temperature at the time of measurement. Accordingly, the wavelengths measured at each temperature are also stored in the database in memory in the computer 17. In the step S13 for determining the measurement window at each temperature shown in FIG. 1, the peak wavelengths P20, P21, P22, and P23, which are the maximum intensities of the spectra R20E, R21E, R22E, and R23E of reflected light from the sensor part embedded in the adhesive 32, are determined as the measurement wavelengths (measurement windows). The peak wavelengths P20, P21, P22, and P23 thereof are then stored in the database.

The database is thus created in the above manner.

Next, the actual peeling inspection step S2 for the adhesive 32 will be described with reference to FIG. 10.

Figure 10:
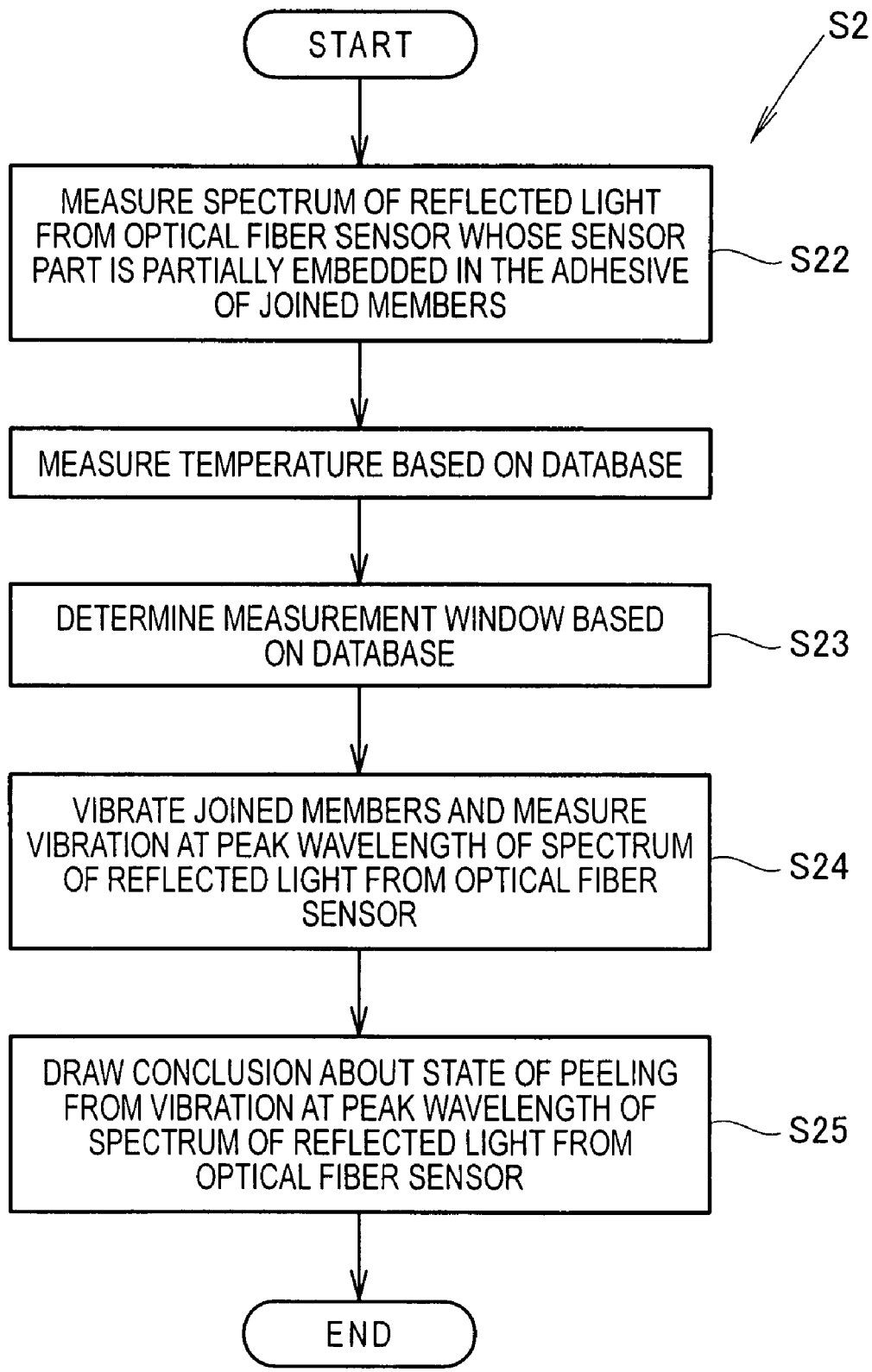
FIG. 10 is a flowchart describing the step for inspecting peeling in the adhesive joint.

FIG. 10 shows the peeling inspection step S2 for the adhesive 32. The peeling inspection step S2 for the adhesive 32 is composed of a measuring step S21 for measuring the reflection spectrum from the optical fiber sensor 35 whose sensor part 35s is embedded in the adhesive 32 of the joined members, a measuring step S22 for measuring the temperature on the basis of the database, a determination step S23 for determining the measurement window on the basis of the database, a measuring step S24 for vibrating the joined members to measure vibration at the peak wavelength of the spectrum of reflected light from the optical fiber sensor 35, and a conclusion step S25 for drawing a conclusion about the state of peeling from the vibration at the peak wavelength of the spectrum of reflected light from the optical fiber sensor 35.

Step S21 for measuring the reflection spectrum from the optical fiber sensor 35 uses an apparatus configuration that is identical to the measurement system shown in FIG. 6, except that the thermostat 14 is not used. Half of the sensor part 35s of the optical fiber sensor 35 is embedded in the adhesive 32 of the adhesive joint 33 between the joined members (the members 30, 31) measured under actual conditions. The measurement method is the same as the method performed at the time the database was created. As an example, it is assumed that the spectrum R21 of reflected light shown in graph (C) in FIG. 9 is obtained.

In the measuring step S22 for measuring the temperature on the basis of the database, the maximum peak wavelength of the spectrum R21F of reflected light from the sensor part not embedded in the adhesive 32 is measured from the spectrum R21 of reflected light obtained in the measuring step S21. The measurement temperature is determined based on the peak wavelength and the data shown in FIG. 5.

For example, the maximum peak wavelength of the spectrum of reflected light in FIG. 9(C) is λ2. Therefore, the spectrum of reflected light from the sensor part 35s of the optical fiber sensor 35, which includes wavelength λ2, coincides with the spectrum R11 of reflected light shown in FIG. 5(C). Therefore, the temperature conditions are determined to be T=57° C.

In the determination step S23 for the measurement window, the measurement window for the next vibration measurement is determined from the measurement temperature on the basis of the database. When, e.g., T=57° C., the wavelength P21 that coincides with the peak according to FIG. 9(C) is used as the measurement window.

Figure 11:
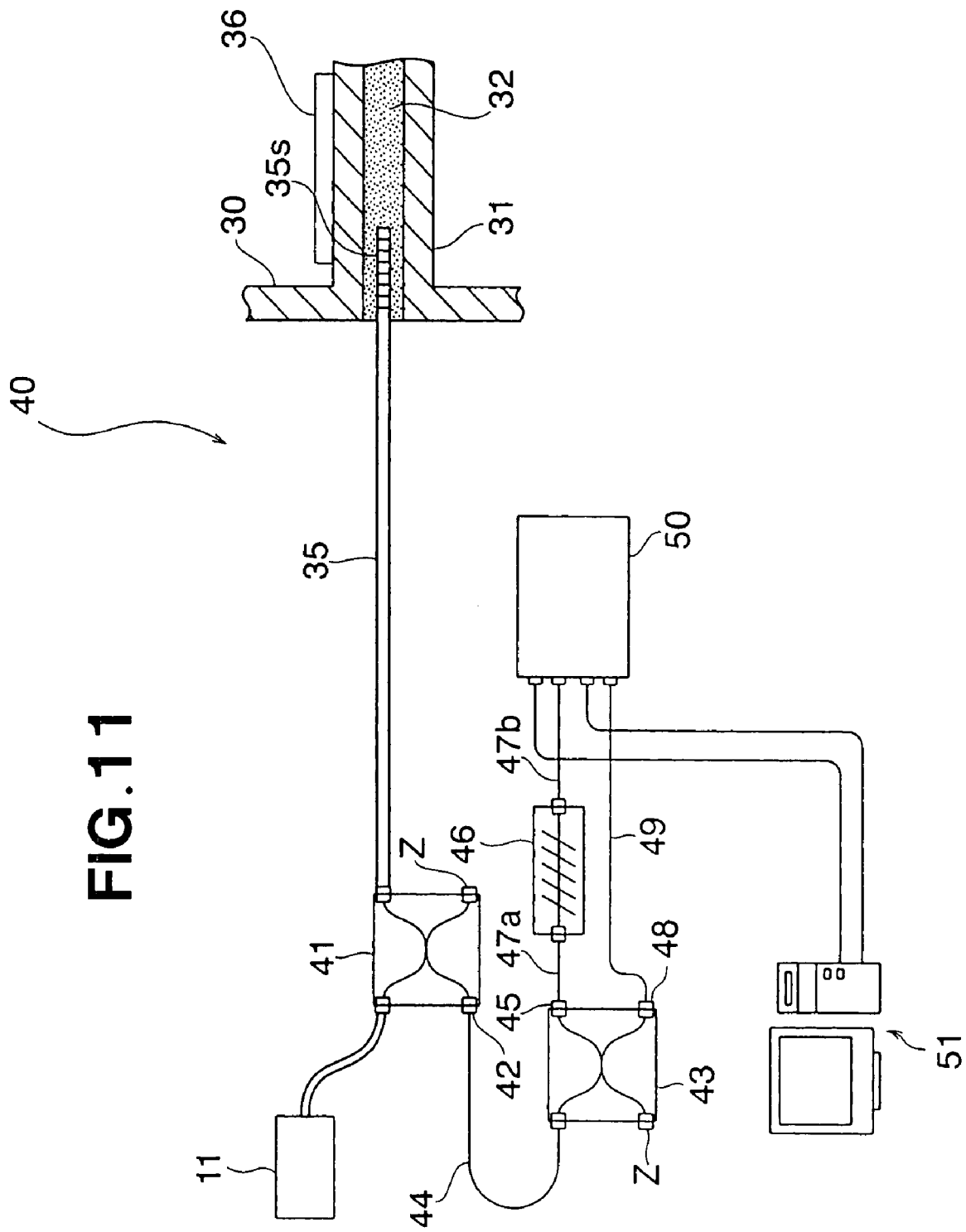
FIG. 11 is a schematic view illustrating a measurement system used in a measuring step for measuring vibration at the peak wavelength of the reflection spectrum from the optical fiber sensor while the joined members are vibrated.

Next, the measurement system used in the measurement step S25 will be described with reference to FIG. 11. In FIG. 11, the same numerical symbols are used to denote elements that are substantially similar to those described above.

The measurement system 40 shown in FIG. 11 is composed of a light source 11, two beam splitters 41, 43, an optical fiber sensor 35 having a sensor part 35s embedded in an adhesive 32 between joined members (members 30, 31), an optical fiber 44 for connecting a terminal 42 of the beam splitter 41 with the beam splitter 43, an optical filter 46, an optical filter 47a for connecting a terminal 45 of the beam splitter 43 with the optical filter 46, a light detector 50, an optical fiber 47b for connecting the optical filter 46 with the light detector 50, an optical fiber 49 for connecting a terminal 48 of the beam splitter 43 with the light detector 50, and a computer 51 connected to the light detector 50. A piezoelectric element 36 as a vibrating device is attached to member 30, which is one of the joined members.

In the optical fiber sensor 35, light from the light source 11 is guided to the sensor part 35s via the beam splitter 41. The reflected light from the sensor part 35s is guided to the beam splitter 43 via the beam splitter 41. Two optical paths are provided on the output side of the beam splitter 43. One optical path is inputted to the light detector 50 through the optical filter 46. The other optical path is inputted directly to the light detector 50. The output from the light detector 50 is inputted to the computer 51.

For the optical filter 46, an optical filter is used that transmits light whose wavelength matches the one corresponding to the measurement window determined in step S23, and does not transmit light with any other wavelength. It is assumed in this case that the temperature T is 57° C., and the wavelength P21 is used as the measurement window. Specifically, an optical filter is used that transmits light with a wavelength P21 and does not transmit light with any other wavelength.

Next, the measurement method (peeling detection method) based on the measurement system 40 will be described.

Broadband light outputted from the light source 11 is directed to the optical fiber sensor 35. Light reaches the sensor part 35s of the optical fiber sensor 35 from the beam splitter 41, and the reflected light reaches the second beam splitter 43. The beam splitter 43 separates this light into light that reaches the light detector 50 through the optical filter 46, and light that reaches the light detector 50 directly. The light detector 50 detects the ratio of the intensities of these two beams of light on the basis of the two beams of light sent from the beam splitter 43. The variation in the center wavelength of the sensor part 35s is measured based on the ratio of light intensities detected by the light detector 50.

In the measurement system 40, when the piezoelectric element 36, 25 which is a vibrating device, is operated to vibrate the joined members (the members 30, 31), the sensor part 35s embedded in the adhesive 32 of the optical fiber sensor 35 expands and contracts. At this time, the spectrum of reflected light from the optical fiber sensor 35 varies along with the expansion and contraction of the sensor part 35s. The corresponding output from the light detector 50 undergoes vibration as well. At this time, the variation in wavelength is measured as a variation in voltage.

When vibration is induced in the joined members (the members 30, 31) by the piezoelectric element 36, the sensor part 35s embedded in the adhesive 32 also vibrates, and the interval of the diffraction grating of the sensor part 35s fluctuates along with this vibration. The peak wavelength of the spectrum of reflected light is thereby caused to vibrate as well. When peeling occurs in the adhesive 32 of the joined members, the members 30, 31 lose rigidity, and the vibration is greater than the induced vibration. Fluctuation of the intervals of the diffraction grating of the sensor part 35s is thereby increased, and there is increased vibration in the peak wavelength of the spectrum of reflected light. By measuring the vibration at the peak of the spectrum of reflected light, it is concluded that peeling has occurred in the adhesive joint 33 when the amplitude of vibration is greater than a specific amplitude value.

Figure 12A:
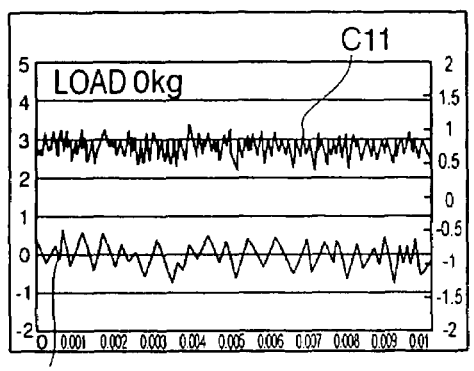
FIG. 12A is a graph showing vibration at the peak wavelength of the reflection spectrum when the joined members are vibrated under actual conditions, and also showing vibration at the peak wavelength when the vibrating device is driven in a load-free state without any peeling.
Figure 12B:
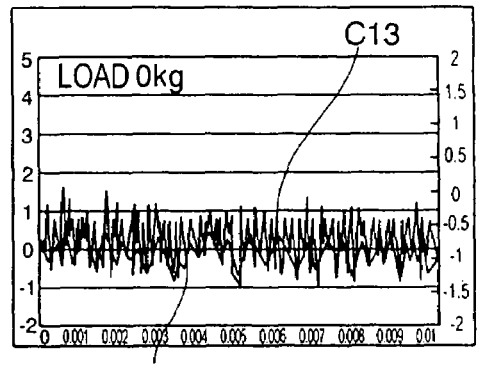
FIG. 12B is a graph showing vibration at the peak wavelength of the reflection spectrum when the joined members are vibrated under actual conditions, and also showing the varying characteristics of the peak wavelength when 8 mm of peeling have occurred.

FIGS. 12A and 12B are graphs showing vibration at the peak wavelength P21 of the spectrum of reflected light when vibration is induced under actual conditions in the joined members. FIG. 12A shows vibration occurring at the peak wavelength P21 when the piezoelectric element 36 (vibrating device) is driven in a load-free state without any peeling. In FIG. 12A, the horizontal axis represents time, and the vertical axis represents voltage. The graph shows the varying waveform and other characteristics of the wavelength. The waveform C10 represents variation in the voltage applied to the piezoelectric element 36, and the waveform C11 represents variation in the peak wavelength. FIG. 12B is similar to FIG. 12A, and shows the varying waveform of the peak wavelength when 8 mm of peeling have occurred. The waveform C12 represents variation in the voltage applied to the piezoelectric element 36, and the waveform C13 represents vibration at the peak wavelength P21. It can be seen that when peeling occurs, the amplitude of vibration at the peak wavelength increases to nearly two times.

Figure 13A:
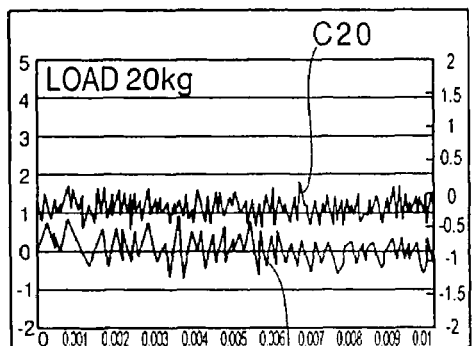
FIG. 13A is a graph showing variation in the peak wavelength when the vibrating device is driven while a load is applied to the joined members, and also showing the varying characteristics when there is no peeling.
Figure 13B:
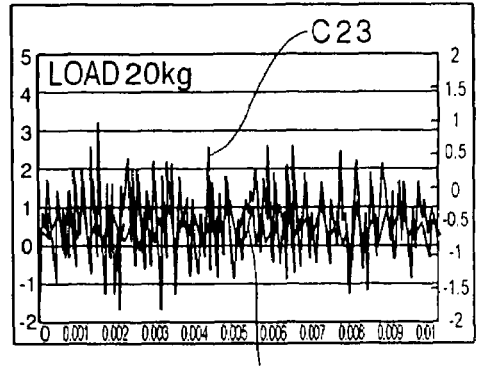
FIG. 13B is a graph showing variation in the peak wavelength when the vibrating device is driven while a load is applied to the joined members, and also showing the varying characteristics when there is peeling.

FIGS. 13A and 13B are similar to FIGS. 12A and 12B, respectively, and are graphs showing the vibration at the peak wavelength P21 of the spectrum of reflected light when vibration is induced under actual conditions in the joined members while a load (such as a load of pulling the two members 30, 31 apart) of, e.g., 20 kg is applied. FIG. 13A shows a case of no peeling, wherein the waveform C20 represents variation in the voltage applied to the piezoelectric element 36, and the waveform C21 represents vibration at the peak wavelength P21. FIG. 13B is similar to FIG. 13A and shows the varying waveform of the peak wavelength when 8 mm of peeling have occurred. The waveform C22 represents variation in the voltage applied to the piezoelectric element 36, and the waveform C23 represents vibration at the peak wavelength P21. It can be seen that when peeling occurs, the amplitude of vibration at the peak wavelength increases nearly fivefold.

It can be seen that when peeling occurs in the adhesive joint 33 as described above (the examples shown in FIGS. 12B and 13B), the amplitude of vibration at the peak wavelength is greater than when peeling has not occurred. It can thereby be concluded that peeling has occurred in the adhesive joint 33 when vibration is induced in the joined members and the vibration of the peak wavelength increases. It can also be seen that when a step for applying a specific load (20 kg, for example) to the joined members is added to the step for vibrating the joined members with the aid of the piezoelectric element 36, vibration is obtained wherein the joined members vibrate at a greater amplitude in cases in which peeling occurs in the adhesive joint 33. Generally, the specific load is preferably an external force that elastically deforms the joined members composed of the two members 30, 31 joined using the adhesive 32.

Figure 14:
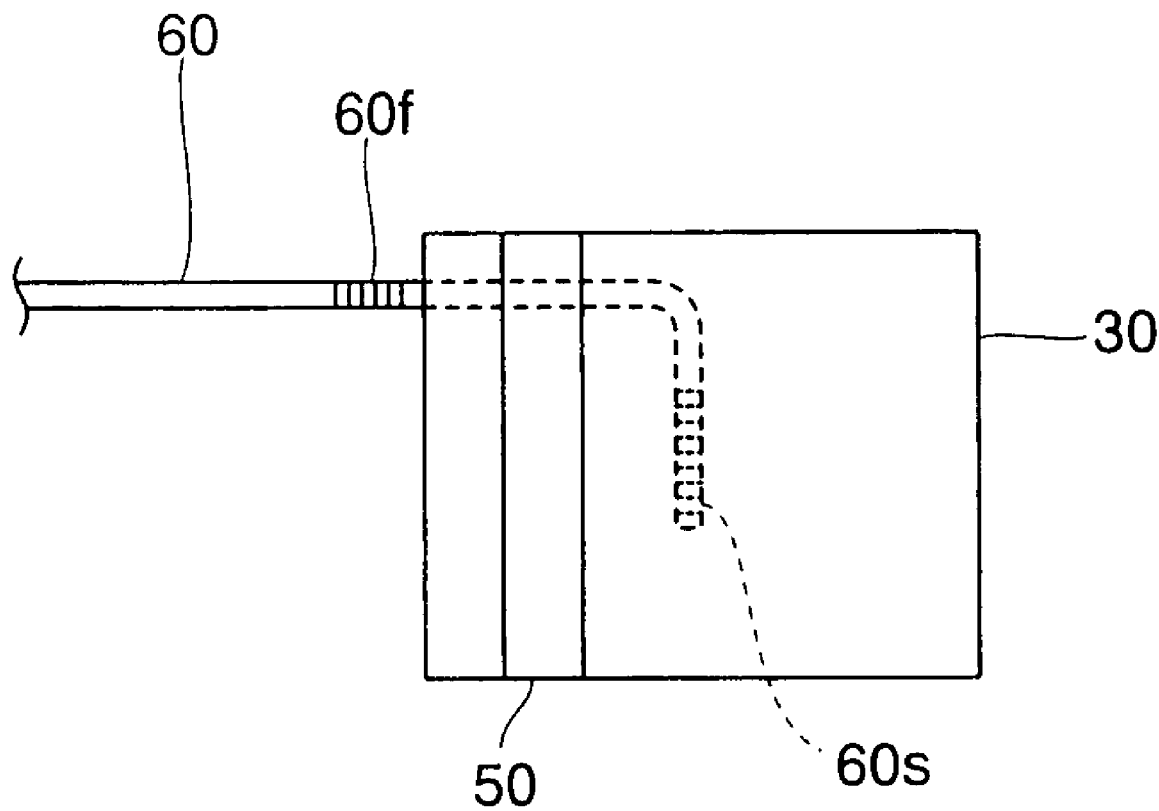
FIG. 14 is a schematic view of another embodiment of the present invention, which is a case in which the sensor part is embedded parallel to the peeling direction (the border line between the peeling part and the non-peeling part)

FIG. 14 shows the embedded structure of a sensor part of an optical fiber sensor used in a measurement system according to another embodiment. In this embodiment, the sensor part embedded in the adhesive 32 is disposed parallel to the longitudinal direction of the area in which peeling occurs. FIG. 14 shows an area of the previously described member 30 shown in a plan view, in which peeling occurs in a belt-shaped area denoted by the reference numeral 50. The optical fiber sensor 60 used in the measuring system in this embodiment is provided with two sensor parts 60f, 60s. The sensor part 60f formed in the middle of the optical fiber sensor 60 is located on the outside of the member 30, i.e., on the outside of the previously described adhesive 32. In the optical fiber sensor 60, the portion at the distal end shown by the dotted lines in FIG. 14 represents the portion embedded in the adhesive 32. In the portion farther out to the distal end than the sensor part 60f, the distal end is bent into a substantial right angle so as to be parallel to the belt-shaped peeling area 50. The sensor part 60s is formed at the bent distal end of the optical fiber sensor 60. The sensor part 60s is parallel to the longitudinal direction (peeling direction) of the belt-shaped peeling area 50. The sensor part 60s is located inside the adhesive 32. Since a plan view of the member 30 is shown in FIG. 14, the portion of the optical fiber sensor 60 embedded in the adhesive 32 is shown in dotted lines on the member 30.

Figure 15A:
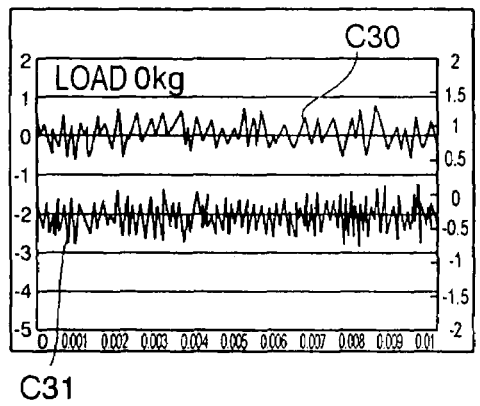
FIG. 15A is a graph showing vibration at the peak wavelength of the reflection spectrum when the joined members are vibrated under actual conditions, and also showing vibration characteristics in the peak wavelength when the vibrating device is driven in a load-free state without any peeling.
Figure 15B:
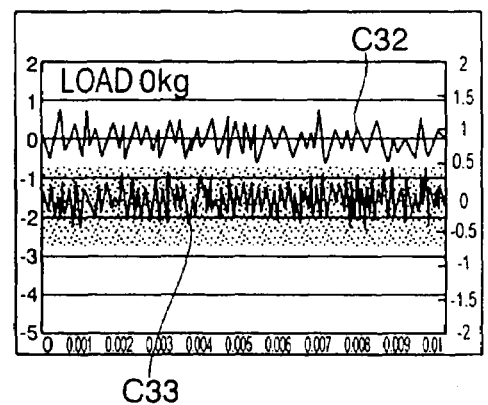
FIG. 15B is a graph showing variation in the peak wavelength of the reflected light when the joined members are vibrated under actual conditions, and also showing the varying characteristics of the peak wavelength when 8 mm of peeling have occurred.

The results of the peeling measurement method based on the measurement system according to another embodiment are described with reference to FIGS. 15A, 15B, 16A, and 16B. FIGS. 15A and 15B correspond to FIGS. 12A and 12B, respectively; and FIGS. 16A and 16B correspond to FIGS. 13A and 13B, respectively. The load in FIGS. 16A and 16B is 40 kg, for example.

FIG. 15A shows the vibration characteristics of the peak wavelength P21 obtained when the piezoelectric element 36 is driven in a load-free state without any peeling in the measurement system based on the other embodiment. The waveform C30 represents variation in the vibration voltage applied to the piezoelectric element 36, and the waveform C31 represents the vibration waveform of the peak wavelength. FIG. 15B shows the vibration characteristics of the peak wavelength P21 when 8 mm of peeling have occurred. The waveform C32 represents variation in the vibration-inducing voltage, and the waveform C33 represents the vibration waveform of the peak wavelength P21. The amplitude of the waveform 33 is 1.55 times the amplitude of the waveform 31.

Figure 16A:
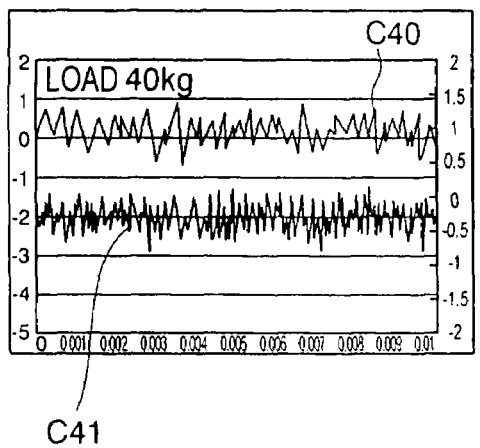
FIG. 16A is a graph showing variation in the peak wavelength when the vibrating device is driven while a load of 20 Kgf is applied to the joined members, and also showing the varying characteristics when there is no peeling.
Figure 16B:
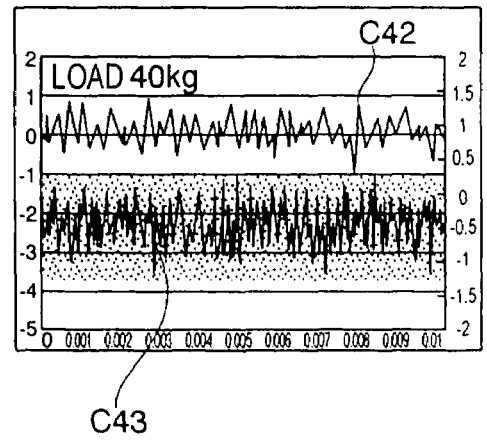
FIG. 16B is a graph showing variation in the peak wavelength when the vibrating device is driven while a load of 20 Kgf is applied to the joined members, and also showing the varying characteristics when there is peeling.

FIG. 16A shows a case of no peeling with a load of 40 kg in a measurement system based on the other embodiment, wherein the waveform C40 represents variation in the vibration voltage applied to the piezoelectric element 36, and the waveform C41 represents the vibration characteristics of the peak wavelength P21. FIG. 16B shows the vibration characteristics of the peak wavelength with a load of 40 kg and 8 mm of peeling in a measurement system based on the other embodiment. The waveform C42 represents variation in the vibration-inducing voltage, and the waveform C43 represents the vibration characteristics of the peak wavelength P21. It can be seen that when peeling occurs, the amplitude of the vibration characteristics of the peak wavelength P21 increases to 1.67 times.

As described above, it can be seen that vibration at the peak wavelength increases as shown in FIGS. 15A, 15B, 16A, and 16B. It can thereby be concluded that peeling occurs in the adhesive 32 in cases in which vibration in the joined members (the member 30) is induced by the piezoelectric element 36 and the amplitude increases in the vibration characteristics of the peak wavelength.

The configurations, shapes, sizes, and positional relationships described in the above embodiments are merely depicted schematically to the extent that would allow the present invention to be understood and implemented, and the numerical values and compositions (materials) of structures are merely examples. Therefore, the present invention is not limited to the embodiments described above, and various modifications can be made as long as these modifications do not deviate from the scope of the technological ideas presented in the claims.

Obviously, various minor changes and modifications of the present invention are possible in light of the above teaching. It is therefore to be understood that within the scope of the appended claims the invention may be practiced otherwise than as specifically described.

What is claimed is:

1. A peeling inspection method wherein at least one member selected from at least two members joined using an adhesive is provided with vibration means, a portion of a sensor part of an optical fiber sensor is embedded in the adhesive for joining the two members, and peeling in an adhesive joint of the two or more members is detected on the basis of optical characteristics from the optical fiber sensor when the optical fiber sensor is irradiated with light from a light source while the member is vibrated by the vibration means, the method comprising the steps of:
    determining a temperature of the two members during measurement on the basis of the optical characteristics from that portion of the sensor part which is exposed outside of the adhesive;
    determining, based on the temperature determined during the measurement, a measurement range in which the optical characteristics from the optical fiber sensor are measured;
    vibrating the member by means of the vibration means; and
    measuring the variation in the optical characteristics from the optical fiber sensor within the determined measurement range while the member is being vibrated by the vibration means.

2. The method of claim 1, further comprising a step for applying a specific load from the member side, which step is performed together with the vibrating step.

3. The method of claim 2, wherein the specific load comprises an external force that elastically deforms the joined members composed of at least two members joined using the adhesive.

4. The method of claim 1, wherein the optical fiber sensor comprises an optical fiber grating sensor.

5. The method of claim 1, wherein the optical characteristics comprises reflected light characteristics.

6. The method of claim 1, wherein the adhesive comprises a room-temperature curing adhesive.

7. A method for detecting peeling of two joined members, comprising:
    providing a first database of an optical characteristic of a sensor not embedded in adhesive at various temperatures;
    providing a second database of the measured optical characteristic of a sensor embedded in adhesive at various temperatures; and
    measuring the optical characteristic of a sensor not embedded in adhesive joining two members;
    determining a temperature from the measured optical characteristic based on the first database;
    choosing a measurement window for an embedded sensor for the determined temperature from the second database;
    vibrating the joined members and measuring an optical characteristic of the embedded sensor; and
    determining a state of peeling between the two joined members by comparing the measured optical characteristics of the embedded sensor being vibrated and the chosen measurement window.

8. The method of claim 7, wherein the optical characteristic is the spectrum of reflected light from an optical fiber sensor.

9. A method for detecting peeling of two joined members, comprising:
    measuring temperature;
    choosing a measurement window from a database of an optical characteristic of a sensor embedded in adhesive between two joined members for the measured temperature;
    vibrating the joined members and measuring the optical characteristic of a sensor embedded in the adhesive between the two joined members; and
    determining the state of peeling between the two joined members by comparing the chosen measurement window to the measured optical characteristic of the embedded sensor being vibrated.

10. The method of claim 9, wherein the optical characteristics is the spectrum of reflected light from an optical fiber sensor.

11. The method of claim 9, further comprising
    measuring the temperature by measuring an optical characteristic of a sensor not embedded in adhesive between the joined members at various temperatures;
    creating a database of the optical characteristic of a sensor not embedded in adhesive between the joined members for each temperature;
    measuring the optical characteristic of a sensor not embedded in adhesive between the joined members at various temperatures at an unknown temperature; and
    determining the temperature by comparing the optical characteristic of a sensor not embedded in adhesive between the joined members at various temperatures at an unknown temperature with the database of the optical characteristic of a sensor not embedded in adhesive between the joined members at various temperatures.

* * * * *